United States Patent
Grathwohl (10) Patent No.: US 8,257,342 B2
(45) Date of Patent: Sep. 4, 2012

(54) DUAL LUMEN GASTROINTESTINAL FEEDING AND ASPIRATING DEVICE

(76) Inventor: Kurt W. Grathwohl, McQueeney, TX (US)

( * ) Notice: Subject to any disclaimer, the term of this patent is extended or adjusted under 35 U.S.C. 154(b) by 491 days.

(21) Appl. No.: 12/275,572

(22) Filed: Nov. 21, 2008

(65) Prior Publication Data

US 2009/0156984 A1 Jun. 18, 2009

Related U.S. Application Data

(62) Division of application No. 11/838,657, filed on Aug. 14, 2007.

(51) Int. Cl.
*A61M 31/00* (2006.01)
(52) U.S. Cl. ............ 604/516; 604/27; 604/43; 604/118; 604/514
(58) Field of Classification Search ............... 604/27, 604/28, 34, 40–45, 118, 164.01, 270, 508, 604/514, 516, 523
See application file for complete search history.

(56) References Cited

U.S. PATENT DOCUMENTS

| 5,749,889 | A  | * | 5/1998 | Bacich et al. | 606/198 |
| 5,827,243 | A  | * | 10/1998 | Palestrant | 604/524 |
| 6,689,062 | B1 | * | 2/2004 | Mesallum | 600/439 |
| 2003/0149395 | A1 | * | 8/2003 | Zawacki | 604/40 |
| 2004/0167463 | A1 | * | 8/2004 | Zawacki et al. | 604/43 |

* cited by examiner

*Primary Examiner* — Kevin C. Sirmons
*Assistant Examiner* — Emily Schmidt
(74) *Attorney, Agent, or Firm* — Schmeiser, Olsen & Watts LLP (57) ABSTRACT

A dual lumen gastrointestinal feeding and aspirating device includes an aspiration channel which carries a feeding channel. The aspiration channel has a distal opening with a larger size than that of the feeding channel so it can operate more effectively as a stent and accommodate larger sized instruments. The distal end of the aspiration channel is repeatably moveable between open and closed conditions in response to the extension and retraction, respectively, of the instrument therethrough.

25 Claims, 9 Drawing Sheets

DUAL LUMEN GASTROINTESTINAL FEEDING AND ASPIRATING DEVICE

CROSS-REFERENCE TO RELATED APPLICATION

The present application is a divisional of, and claims priority to, U.S. patent application Ser. No. 11/838,657, filed on Aug. 14, 2007, the contents of which are incorporated herein by reference.

BACKGROUND OF THE INVENTION

1. Field of the Invention

This invention relates generally to medical devices used for feeding and aspirating.

2. Description of the Related Art

Gastrointestinal feeding and aspirating devices generally include feeding and aspirating tubes. The feeding tube is used to provide food internally to a patient. Food is provided to nourish the patient, help him or her heal faster and resist infection, which decreases the patient recovery time. The aspirating tube is used to reduce abdominal distention, which occurs when swallowed air accumulates, and too much food is provided internally relative to its rate of spontaneous absorption. Abdominal distention can impair the ability to breathe deeply and adequately cough to clear secretions. Abdominal distention can also cause discomfort and slow down the rate of bowel absorption. A slower rate of bowel absorption causes undernourishment and slows down the healing process, which increases the patient recovery time. Hence, it is desirable to reduce abdominal distention while providing the patient with sufficient nourishment to facilitate his or her recovery.

There are several different types of feeding and aspirating devices in use, several of which are disclosed in U.S. Pat. Nos. 6,881,211, 6,921,396, and 5,807,311. The feeding and aspirating devices in these disclosures, however, make no provisions for placing them beyond the stomach of the patient where absorption is greater and aspiration is more efficient. Further, these devices undesirably restrict the size of available instruments that can pass through them to guide the device to its desired position within the body.

BRIEF SUMMARY OF THE INVENTION

The present invention employs a dual lumen gastrointestinal feeding and aspirating device ("dual lumen device"), which includes separate aspiration and feeding tubes. The aspiration tube serves as a stent which allows the insertion of a medical instrument into the patient. The aspiration tube has a sufficiently large lumen to allow the insertion of a medical instrument into the patient. The aspiration tube has a distal end repeatably moveable between open and closed conditions in response to the extension and retraction, respectively, of the medical instrument through it.

In one embodiment, windows are positioned proximate to the distal end of the aspiration tube. The windows move away from each other in response to the movement of the instrument from a retracted position to an extended position. The distal end of the aspiration tube moves to its open condition in response to the advancement of the instrument. The windows move towards each other and collapse in response to suction provided by moving the instrument from its extended position to its retracted position. When the windows collapse, the distal opening of the aspiration tube is effectively occluded.

In another embodiment, a one-way valve is connected to the aspiration tube proximate to its distal end. The distal end of the aspiration tube is moved between its open and closed conditions in response to activating and deactivating, respectively, the one-way valve. The one-way valve is activated and deactivated in response to the extension and retraction, respectively, of the instrument through it.

The aspiration tube has a larger cross-sectional area than the feeding tube. In this way, the aspiration tube can accommodate a larger size medical instrument than the feeding tube. In some embodiments, the cross-sectional area of the aspiration tube is circularly shaped and the cross-sectional area of the feeding tube is crescent shaped. The feeding tube can terminate before, at or beyond the distal end of the aspiration tube.

The present invention provides a method, which includes inserting a dual lumen device into a patient, the dual lumen device including a first tube which carries a second tube, the first tube having a larger sized distal opening than the second tube and moving an instrument through the first tube, wherein the distal opening of the first tube moves between deployed and collapsed conditions in response to movement of the instrument. The method can include many other steps. For example, in some embodiments, the method includes collapsing the distal opening of the first tube with suction provided by movement of the instrument.

The dual lumen device can include many other features. For example, in some embodiments, the distal opening of the first tube is spaced a distance from the distal opening of the second tube. In some embodiments, the size of the distal opening of the second tube is too small to accommodate extending the instrument through it. In some embodiments, the first tube includes a window positioned proximate to a distal end of the first tube. In these embodiments, the method can include collapsing the window in response to movement of the instrument.

The present invention provides a method which includes providing a dual lumen device, the dual lumen device including an aspiration tube which carries a feeding tube, wherein the aspiration tube includes a window positioned proximate to its distal end. The method includes inserting the dual lumen device into a patient and moving an instrument through the aspiration tube, wherein the window moves between deployed and collapsed conditions in response to movement of the instrument.

The dual lumen device can include many other features. For example, in some embodiments, the dual lumen device includes a distal opening of the aspiration tube moves between deployed and collapsed conditions in response to the window moving between deployed and collapsed conditions, respectively. In some embodiments, the distal end of the aspiration tube moves between open and closed conditions in response to the window moving between the deployed and collapsed conditions, respectively. In some embodiments, a distal opening of the feeding tube is tapered. In some embodiments, the distal opening of the aspiration tube is spaced from the distal opening of the feeding tube. In some embodiments, the width of the instrument is too large to extend through the feeding tube.

The present invention provides a method, which includes providing a dual lumen device, the dual lumen device including an aspiration and feeding tube and inserting the dual lumen device into a patient. The method includes moving an instrument through the aspiration tube, a distal opening of the aspiration tube moving between open and closed conditions in response to movement of the instrument, wherein the instrument has a dimension which prevents it from extending through a distal opening of the feeding tube.

The dual lumen device can include many other features. For example, in some embodiments, the aspiration tube includes opposed windows positioned proximate to its distal end. The opposed windows typically move between deployed and collapsed conditions in response to movement of the instrument. The opposed windows move towards and away from each other in response to movement of the instrument. In some embodiments, the distal opening of the aspiration tube moves between deployed and collapsed conditions in response to the window moving between deployed and collapsed conditions, respectively. In some embodiments, the aspiration tube includes a plurality of aspirating orifices. In some embodiments, the distal opening of the aspiration tube is spaced from the distal opening of the feeding tube. In some embodiments, the opposed windows are positioned past the distal end of the feeding tube.

These and other features, aspects, and advantages of the present invention will become better understood with reference to the following drawings and description.

DETAILED DESCRIPTION OF THE INVENTION

Figure 1:
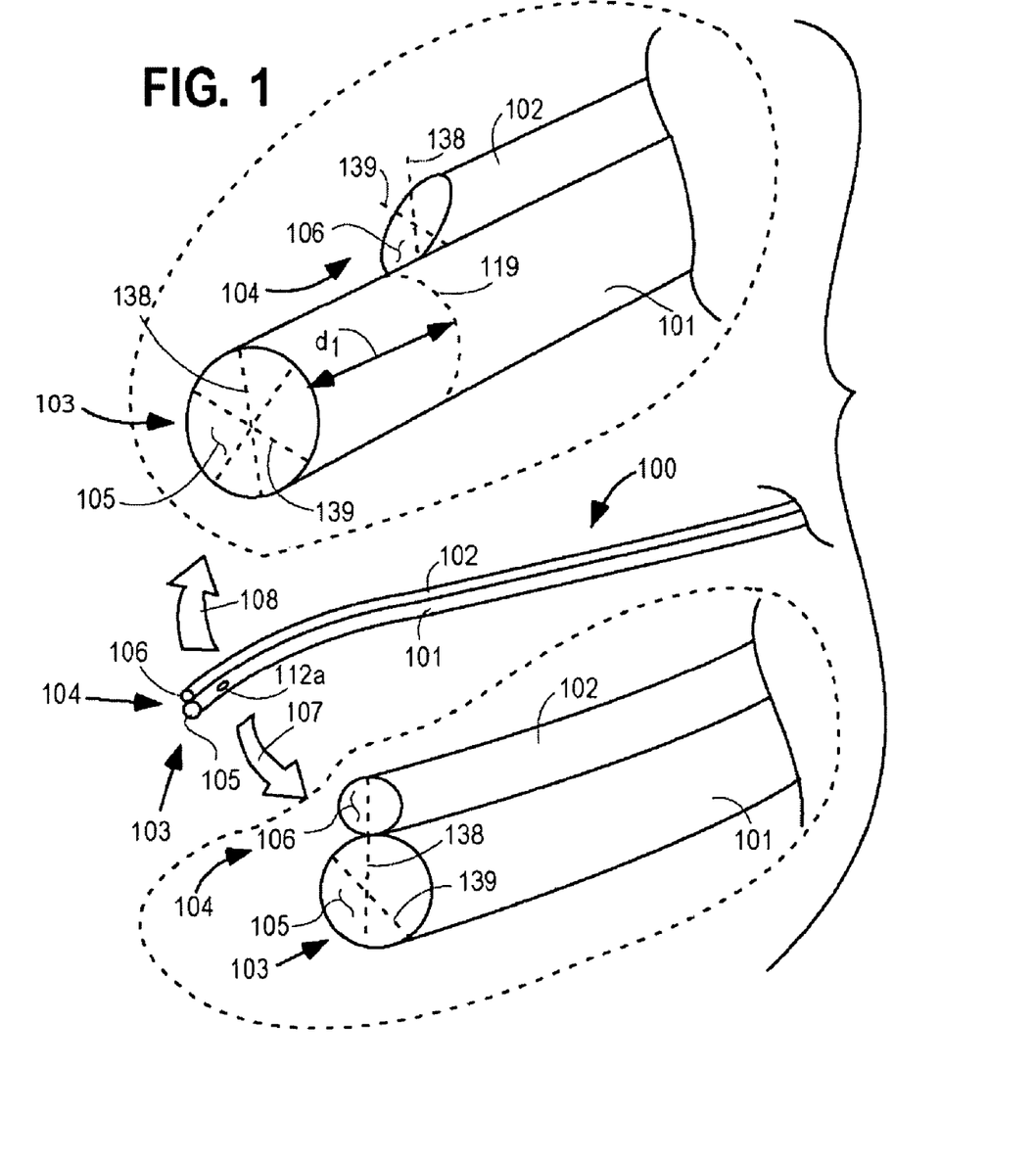
FIG. 1 is a perspective view of a dual lumen gastrointestinal feeding and aspirating device, in accordance with the invention.

FIG. 1 is a perspective view of a dual lumen gastrointestinal feeding and aspirating device 100, in accordance with the invention. In this embodiment, dual lumen device 100 includes an aspiration tube 101 which carries a feeding tube 102. Here, tubes 101 and 102 operate as aspiration and feeding channels, respectively. It should be noted that device 100 is shown here as being a single integrated piece, but it can be separate pieces in other embodiments. For example, tubes 101 and 102 can be separate tubes coupled together. In other embodiments, device 100 is a single tube having separate feeding and aspiration channels extending through it. More information regarding feeding and aspiration channels can be found in U.S. Pat. Nos. 4,543,089 and 4,642,092 by Moss, both of which are incorporated herein by reference.

In accordance with the invention, aspiration tube 101 also operates as a stent for the insertion of an instrument into a patient, as discussed in more detail below. The instrument can be of many different types, but it is generally a medical instrument, such as an angioscope and gastroscope. The instrument is elongated so its distal end can be moved through tube 101 between locations internal and external to the patient. The instrument also has a width dimension, which generally corresponds to its diameter, which determines if it will extend through tubes 101 and 102.

It should be noted that, in general, a larger dimensioned instrument operates better and provides more functionality than a smaller dimensioned one. For example, a larger diameter angioscope has enough room to include better optics, which can provide higher resolution images of the internal condition of the patient. A larger diameter instrument also has more room to include more electronics, such as sensors, which provide information regarding the internal condition of the patient.

Figure 5:
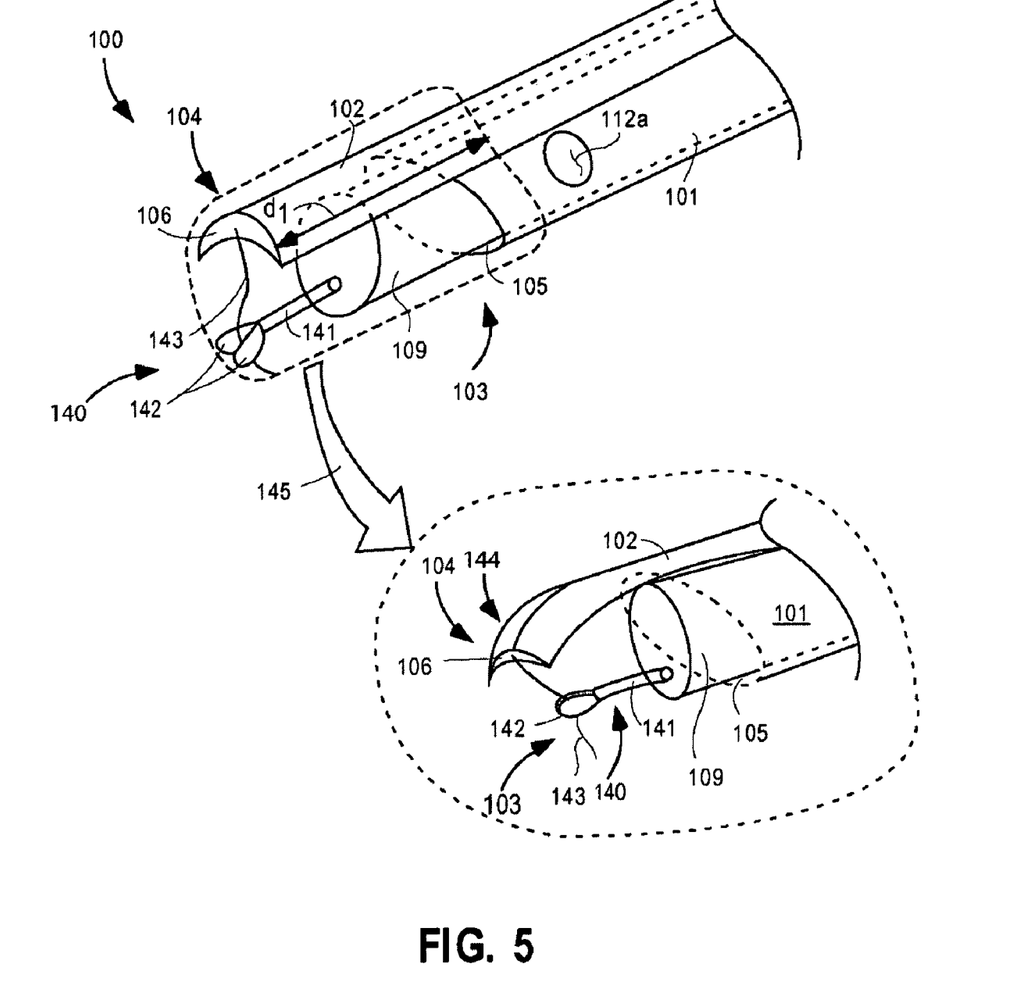
FIG. 5 is a perspective view of another embodiment of a dual lumen device, in accordance with the invention.

Tubes 101 and 102 are connected together lengthwise so their respective distal ends 103 and 104 are positioned proximate to each other. Distal ends 103 and 104 include distal openings 105 and 106, respectively. In some embodiments, distal ends 103 and 104 are positioned adjacent to each other, as indicated by a substitution arrow 107, and in other embodiments, distal end 104 is spaced a distance $d_1$ from distal end 103, as indicated by a substitution arrow 108. FIG. 5 shows an embodiment wherein distal end 104 extends beyond distal end 103 by distance $d_1$. In this way, distal ends 103 and 104 can be even with or spaced apart from each other.

It is useful in some situations to have distal end 104 spaced apart from distal end 103 to reduce the likelihood of having food matter provided by tube 102 interfere with the operation of the instrument extending through tube 101. It is also useful in some situations to have distal end 104 spaced apart from distal end 103 to reduce the amount of material aspirated by aspiration tube 101. This material can be of many different types, but it is generally the food matter flowed into the patient through feeding tube 102. The food matter is often in liquid form, but it can also include solid food matter mixed therein.

For reference purposes, a reference line 119 extends around the outer periphery of tube 101 and, in this embodiment, intersects the outer periphery of opening 106 closest to distal end 103. In this way, distance $d_1$ extends from distal end 103 to reference line 119. Further, a reference line 138 extends between opposed sides of opening 105 and through its center so it bisects tube 101. Reference line 138 is also aligned with the center of opening 106, as best seen in the embodiment indicated by substitution arrow 107, so it bisects tube 102 as well. A reference line 139 is shown extending perpendicular to reference line 138 and through the center of tube 101 so line 139 bisects tube 101. It should be noted that other reference lines can be used and positioned at different locations, but reference lines 138 and 139 are used here for illustrative purposes.

Distal openings 105 and 106 can have many different orientations. In this embodiment, distal openings 105 and 106 extend parallel with each other and reference lines 138 and 139, so that distal ends 103 and 104 are flat. In this way, their cross-sections extend in the plane defined by reference lines 138 and 139. In other embodiments, one or both of distal openings 105 and 106 can extend at an angle with each other, so distal ends 103 and/or 104 are tapered. For example, as indicated by substitution arrow 108, distal opening 106 is at an angle relative to distal opening 105 so its cross-section extends at an angle relative to the length of tube 102 and end 104 is tapered. It should be noted that distal openings 105 and 106 can have many different shapes, as will be discussed in more detail presently.

In this embodiment, distal ends 103 and 104 are flat so distal openings 105 and 106 are circular in shape and define circular cross-sectional areas. When distal end 103 is in its open condition, distal opening 105 is deployed and defines a circular cross-sectional area. When distal end 103 is in its closed condition, distal opening 105 is collapsed and defines a non-circular cross-sectional area. The open and closed conditions are shown in FIGS. 2a-2d, 3a-3b and 4a-4b, and will be discussed in more detail below.

In the embodiment when distal ends 103 and 104 are tapered, distal openings 105 and 106 are elliptical in shape and define elliptical cross-sectional areas. When distal end 103 is in its open condition, elliptical distal opening 105 is deployed and defines an elliptical cross-sectional area. When distal end 103 is in its closed condition, elliptical distal opening 105 is collapsed and defines a non-elliptical cross-sectional area. It should be noted that more matter can flow through a distal opening that is deployed than one that is collapsed. Further, less matter can flow through a distal opening that is collapsed then one that is deployed. It should also be noted that distal openings 105 and 106 can have other shapes. For example, as shown in FIG. 5, distal opening 106 is crescent shaped.

In accordance with the invention, tubes 101 and 102 have different sized distal openings, although distal opening 106 can be the same size as distal opening 105 or larger in some embodiments. One embodiment where tubes 101 and 102 have the same size distal openings is when end 103 is flat and end 104 is tapered, as shown by substitution arrow 108. In another embodiment, end 104 can be tapered so that distal opening 106 has a larger size than distal opening 105. However, a larger dimensioned instrument may still not be able to extend through opening 105 because the distance between opposed sides of tube 102 is not large enough. The distance between opposed sides of tube 102 extends parallel with reference line 138.

In this particular embodiment, distal opening 105 has a larger size than distal opening 106. The sizes of distal openings 105 and 106 are determined by their dimensions, which can be characterized in many different ways. For example, if a distal opening has a circular cross-section when deployed, its dimension is generally characterized by its radius and corresponding circular cross-sectional area. If a distal opening has an elliptical cross-section when deployed, its dimension is generally characterized by the major and minor axes of the ellipse, as well as its corresponding elliptical cross-sectional area.

In general, however, a larger amount of material is capable of flowing through a distal opening with a larger dimension than a distal opening with a smaller dimension. A distal opening with a smaller dimension cannot flow as much material as a distal opening with a larger dimension. Further, larger solid material is capable of flowing through a distal opening with a larger dimension than through a distal opening with a smaller dimension.

It should be noted that an instrument with a larger width is capable of extending through a distal opening with a larger dimension. If the dimension of a distal opening is too small, the larger width instrument may not be able to extend through it, which necessitates the use of an instrument having a smaller width. In some situations, it is desirable to treat the patient with a larger width instrument because, as mentioned above, it generally operates better and provides more functionality than instruments with smaller widths. Further, in some situations, it is desirable to treat the patient with two instruments, such as a gastroscope and forceps, wherein the combination of the two instruments generally has a larger width than any one of them alone. Hence, it is useful to be able to use an instrument that can extend through tube 101, but is too wide to extend through tube 102. In this way, tube 101 can be used as a stent which allows the insertion of a larger sized instrument into the patient. It is also useful if distal end 103 can be moved between opened and closed conditions, as mentioned above, to control the amount of material that flows through opening 105. This can be done in several different ways, one of which will be discussed in more detail presently.

Figure 2A:
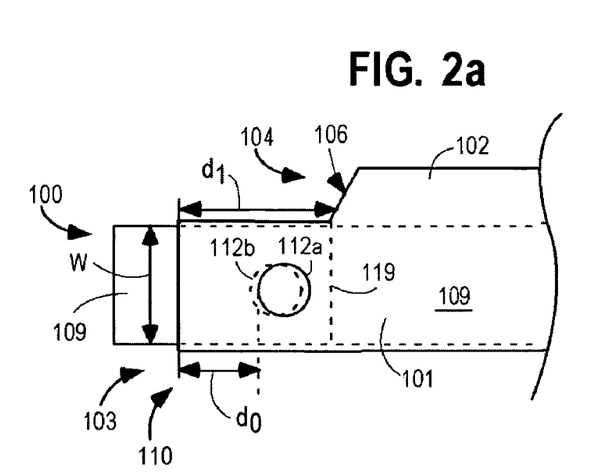
FIGS. 2a and 2b are side views of one embodiment of the dual lumen device of FIG. 1 having opposed windows, in accordance with the invention.
Figure 2B:
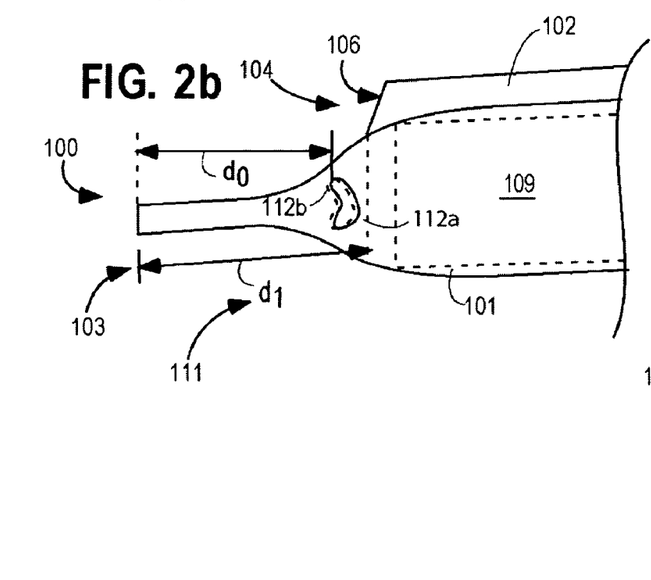

FIGS. 2a and 2b are side views of dual lumen device 100 with an instrument 109 extending through tube 101. Here, the size of distal opening 106 is too small to accommodate extending instrument 109 through it because the width w of instrument 109 is too large. In this embodiment, dual lumen device 100 includes opposed windows 112a and 112b positioned on tube 101 proximate to distal end 103. Opposed windows 112a and 112b are positioned a distance $d_0$ from distal end 103, wherein distance $d_0$ is the distance from distal end 103 to the portion of the outer periphery of windows 112a or 112b closest to it. It should be noted, however, that distance $d_0$ can be the distance from distal end 103 to other portions of windows 112a and 112b, such as their centers. Distances $d_0$ and $d_1$ can have many different values, but they generally have values in a range from about one-half of an inch to three inches. It should also be noted that, as mentioned above, more than one instrument can extend through aspiration tube 101. For example, as shown in FIG. 5, instrument 109, as well as forceps, extend through tube 101.

Here, opposed windows 112a and 112b are circular in shape, but they can have other shapes, such as elliptical, in other embodiments. Opposed windows 112a and 112b define circular cross-sectional areas when in deployed conditions, as shown in FIG. 2a, and non-circular cross-sectional areas when in collapsed conditions, as shown in FIG. 2b. When opposed windows 112a and 112b are elliptical in shape, they define elliptical cross-sectional areas when they are deployed and non-elliptical cross-sectional areas when they are collapsed. A deployed window allows more material to flow through it than a collapsed window and a collapsed window allows less material to flow through it than a deployed window. Hence, a circular window allows more material to flow through it when it has a circular cross-sectional area (i.e. it is deployed) than when it has a non-circular cross-sectional area (i.e. it is collapsed). Further, an elliptical window allows more material to flow through it when it has an elliptical cross-sectional area than when it has a non-elliptical cross-sectional area. It should be noted that window 112b is represented in phantom by a dotted line because it is positioned on tube 101 so it opposes window 112a.

In accordance with the invention, distal end 103 is repeatably moveable between open and closed conditions 110 and 111, as shown in FIGS. 2a and 2b, respectively, in response to the movement of windows 112a and 112b. Windows 112a and 112b move in response to the movement of instrument 109 between extended and retracted positions. In the extended position, instrument 109 terminates outside of tube 101 beyond distal end 103, as shown in FIG. 2a. In the retracted position, instrument 109 terminates inside of tube 101 before distal end 103, as shown in FIG. 2b. Opposed windows 112a and 112b are deployed when distal opening 103 is deployed and windows 112a and 112b are collapsed when distal opening 103 is collapsed.

When instrument 109 moves from the retracted position to the extended position, it engages distal end 103 and opening 105 deploys in response so that distal end 103 is moved to its open condition 110 (FIG. 2a). When instrument 109 moves from the retracted position to the extended position, windows 112a and 112b are pushed away from each other by instrument 109 and they move from collapsed to deployed conditions in response.

When instrument 109 moves from the extended position to the retracted position, it disengages distal end 103 and suction is provided between it and tube 101. The suction pulls windows 112a and 112b towards each other and they, as well as opening 105, move from deployed to collapsed conditions in response (FIG. 2b). The suction can also draw matter, such as food material and mucosa, into tube 101 so it blocks opening 105. Hence, distal opening 105 is moveable between conditions having circular and non-circular cross-sectional areas in response to the movement of instrument 109. The suction is relieved by windows 112a and 112b when instrument 109 moves to a position where it terminates before them in tube 101. Hence, distal end 103 closes in response to suction provided by the movement of instrument 109. In this way, distal opening 103 moves between open and closed conditions 110 and 111 in response to the movement of instrument 109 through tube 101.

When windows 112a and 112b move towards each other, the portion of tube 101 between windows 112a, 112b and distal opening 105 collapses and forms a seal so that distal end 103 is closed. The seal is formed to restrict the flow of matter through distal opening 105. It should be noted that in some situations the portion of tube 101 between windows 112a, 112b and distal opening 105 can collapse around the matter, such as food material and mucosa, drawn into tube 101 in response to the suction.

When windows 112a and 112b move away from each other, the portion of tube 101 between windows 112a, 112b and distal opening 105 deploys and does not form a seal so that distal end 103 is open. When opening 105 is collapsed, less matter is capable of flowing through it. When opening 105 is deployed, more matter is capable of flowing through it. Hence, the flow of matter through distal opening 105 is not restricted when it is deployed and is restricted when it is collapsed. In this way, distal end 103 operates as a one-way valve in response to the movement of windows 112a and 112b.

It should be noted that windows 112a and 112b can be positioned in many different ways on tube 101. For example, the movement of windows 112a and 112b in FIGS. 2a and 2b is substantially parallel to reference line 139 (FIG. 1). Further, distal opening 105 can be biased to deploy and collapse in many different ways. For example, windows 112a and 112b oppose each other in FIGS. 2a and 2b and distal opening 105 is biased to collapse so it extends parallel to reference line 139. These features can be better seen in perspective views of dual lumen device 100, some of which will be discussed in more detail presently.

Figure 2C:
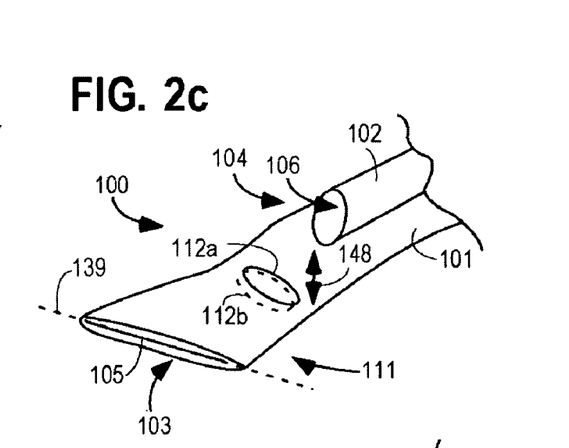
FIGS. 2c and 2d are perspective views of a dual lumen device having opposed windows positioned in different ways.
Figure 2D:
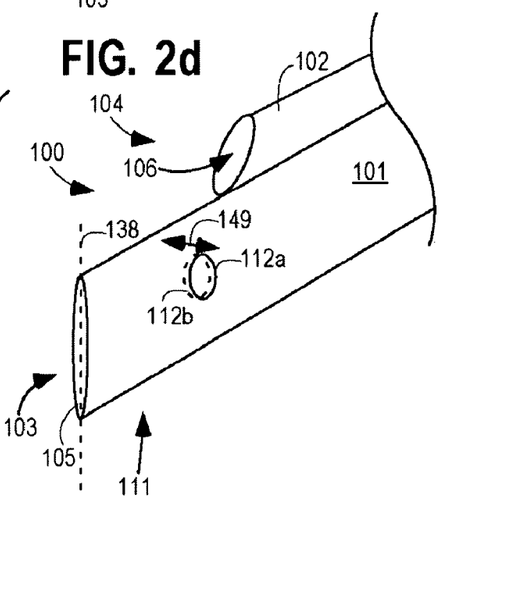

FIGS. 2c and 2d are perspective views of dual lumen device 100 showing other ways that windows 112a and 112b can be positioned and distal opening 105 can be biased. In FIG. 2c, distal opening 105 is biased to extend parallel to reference line 139 when it is collapsed and windows 112a and 112b are positioned to move substantially perpendicular to reference line 139, as indicated by a movement arrow 148. In FIG. 2d, distal opening 105 is biased to extend parallel to reference line 138 when it is collapsed and windows 112a and 112b are positioned to move substantially perpendicular to reference line 138, as indicated by a movement arrow 149. It should be noted that windows 112a and 112b can be positioned, and distal opening 105 can be biased, in other directions relative to reference lines 138 and 139. It should also be noted that windows 112a and 112b are shown as being opposed to each other, although they do not have to be in other embodiments, some of which will be discussed presently.

Figures 3A, 3B, 4A, 4B:
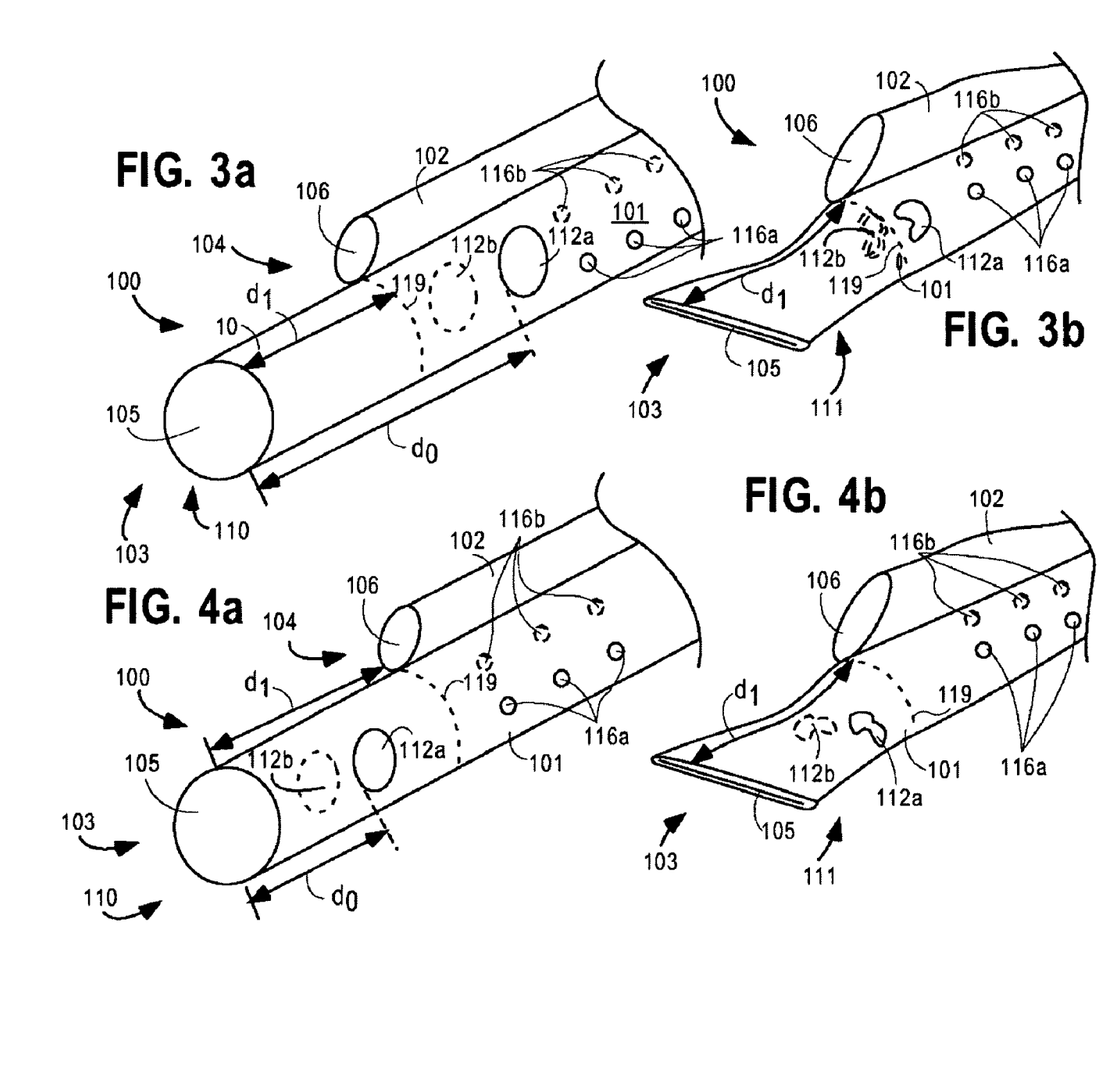
FIGS. 3a and 3b are perspective views of the dual lumen device of FIGS. 2a and 2b, with windows positioned away from its distal end.
FIGS. 4a and 4b are perspective views of the dual lumen device of FIGS. 2a and 2b, with windows positioned towards its distal end.

FIGS. 3a and 3b are perspective views of dual lumen device 100 with distal end 103 in open and closed conditions 110 and 111, respectively, as described above. In this embodiment, windows 112a and 112b are positioned distance $d_0$ away from distal end 103, wherein distance $d_0$ is greater than distance $d_1$. Dual lumen device 100 includes aspirating orifices 116a and 116b which are spaced apart from each other lengthwise along tube 101. Aspirating orifices 116a and 116b are positioned on the same side of reference line 119 as windows 112a and 112b, although some can be positioned on the other side, as will be discussed below. In this embodiment, aspirating orifices have smaller sizes than windows 112a and 112b and windows 112a and 112b have smaller sizes than opening 106. Further, opening 106 has a smaller size than opening 105, as discussed above. Aspirating orifices 116a and 116b allow the aspiration of matter through tube 101 when distal end 103 is in closed condition 111.

FIGS. 4a and 4b are perspective views of another embodiment of dual lumen device 100 with distal end 103 in open and closed conditions 110 and 111, respectively, as described above. In this embodiment, windows 112a and 112b are positioned distance $d_0$ away from distal end 103, wherein distance $d_0$ is less than distance $d_1$. Further, windows 112a and 112b do not oppose each other, although they can overlap when moved together. Dual lumen device 100 includes aspirating orifices 116a and 116b which are spaced apart from each other lengthwise along tube 101. Aspirating orifices 116a and 116b can oppose each other, if desired, and are positioned on the other side of reference line 119 from windows 112a and 112b, although some or all of them can be positioned on the same side.

As shown in FIGS. 3a and 4a, distal opening 105 has a circular cross-sectional area when it is deployed and distal end 103 is in open condition 110. Further, windows 112a and 112b have circular cross-sectional areas when distal end 103 is in open condition 110. As shown in FIGS. 3b and 4b, distal opening 105 has a non-circular cross-sectional area when it is collapsed and distal end 103 is in closed condition 111. Further, windows 112a and 112b have non-circular cross-sectional areas when distal end 103 is in closed condition 111.

The positioning of windows 112a and 112b, as well as aspirating orifices 116a and 116b, are chosen to determine the operation of dual lumen device 100. For example, the positioning of aspiration openings 116a and 116b relative to distal opening 106 affects the amount of matter aspirated through them. The positioning of aspirating orifices 116a and 116b relative to opening 106 determines the rate at which they aspirate food. Aspirating orifices 116a and 116b aspirate food at a faster rate if they are positioned closer to opening 106. Further, aspirating orifices 116a and 116b aspirate food at a slower rate if they are positioned away from opening 106.

The positioning of windows 112a and 112b affects the sealing properties of distal end 103 when in closed condition 111. This is because the portion of tube 101 between distal end 103 and windows 112a and 112b collapses to form the seal when end 103 is in collapsed condition 111. Hence, distance $d_0$ determines how much of tube 101 collapses to form the seal. As distance $d_0$ increases, more of tube 101 collapses and the seal is stronger in response. Further, more matter, such as food material and mucosa, is sealed if more of tube 101 collapses, which also strengthens the seal.

As distance $d_0$ decreases, less of tube 101 collapses and the seal is weaker in response. Further, less matter is sealed if less of tube 101 collapses, which also weakens the seal. It should be noted that, in general, a stronger seal allows less matter to flow through it and a weaker seal allows more matter to flow through it. It should also be noted that distal end 103 can be moved between open and closed conditions 110 and 111 in many other ways, one of which will be discussed presently.

FIG. 5 is a perspective view of another embodiment of dual lumen device 100, in accordance with the invention. In this embodiment, device 100 includes feeding tube 102 carried by aspiration tube 101 as described above. Here, however, distal opening 106 is crescent shaped so it is easier to insert device 100 into the patient. A crescent shaped distal opening 106 makes it easier to insert device 100 into the patient because the distance between the centers of openings 105 and 106 along reference line 138 (not shown) is reduced. By making distal opening 105 crescent shaped, less material is needed to couple tubes 101 and 102 together because they share a larger common area. This is useful because device 100 generally costs less if it includes less material.

Further, distal opening 105 is tapered so it is easier to insert device 100 into the patient. In this embodiment, distal opening 105 is tapered by making its outer periphery near feeding tube 102 closer to distal end 104 than its outer periphery away from feeding tube 102. Here, distal end 104 extends beyond distal end 103 by distance $d_1$ so that feeding tube 102 can extend further into the patient. This is useful when it is desired to extend feeding tube 102 beyond the patient's stomach and into his or her intestinal tract.

In this embodiment, dual lumen device 100 also includes an elongated member 143 coupled to feeding tube 102. Elongated member 143 can be made of many different materials, such as plastic, rubber and string, which are compatible with being inserted into a patient. In this embodiment, member 143 is attached to feeding tube 102 at distal end 104 with an adhesive. However, elongated member 143 can be attached to feeding tube 102 in many different ways and at many different locations. For example, member 143 can be tied to tube 102 at distal end 104 or it can be attached to tube 102 between distal ends 103 and 104. It is useful if elongated member 143 is positioned so it can be grasped with an instrument extending through aspiration tube 101, as will be discussed in more detail presently.

In this embodiment, elongated member 143 can be grasped with forceps 140, which extend through aspiration tube 101, along with instrument 109. Forceps 140 can be of many different types, such as grasping and biopsy forceps. Forceps 140 include an elongated body 141 which extends through aspiration channel 103. Opposing gripping members 142 are operatively coupled to the distal end of elongated body 141 and are moveable between grasping and non-grasping positions.

Grasping members 142 are in their non-grasping position in FIG. 5 wherein they do no grasp elongated member 143. Grasping members 142 are in their grasping positions, as shown in FIG. 5 in an alternative view indicated by a substitution arrow 145. When elongated member 143 is grasped by forceps 141, dual lumen device 100 can be more easily inserted into the patient and removed therefrom.

For example, in one situation, instrument 109 is inserted through aspiration tube 101 before device 100 is inserted into the patient. Forceps 140 are also inserted through aspiration tube 101 and elongated member 143 is grasped by grasping members 142, as indicated by arrow 145. Elongated member 143 is pulled towards distal end 103 so feeding tube 102 is moved as indicated by a movement arrow 144. This facilitates the insertion of dual lumen device 100 into the patient because the portion of feeding tube 102 that extends beyond distal end 103 is less likely to undesirably engage the patient during insertion.

Figure 6A:
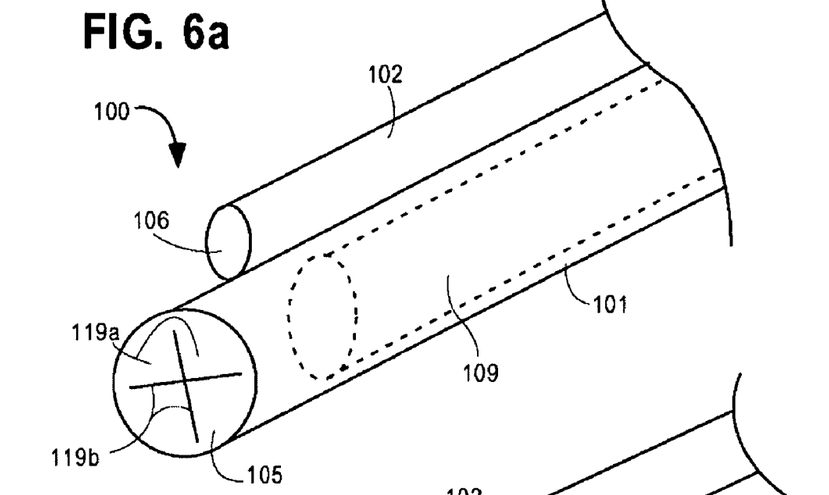
FIGS. 6a and 6b are side views of a dual lumen gastrointestinal feeding and aspirating device having a one-way valve, in accordance with the invention.
Figure 6B:
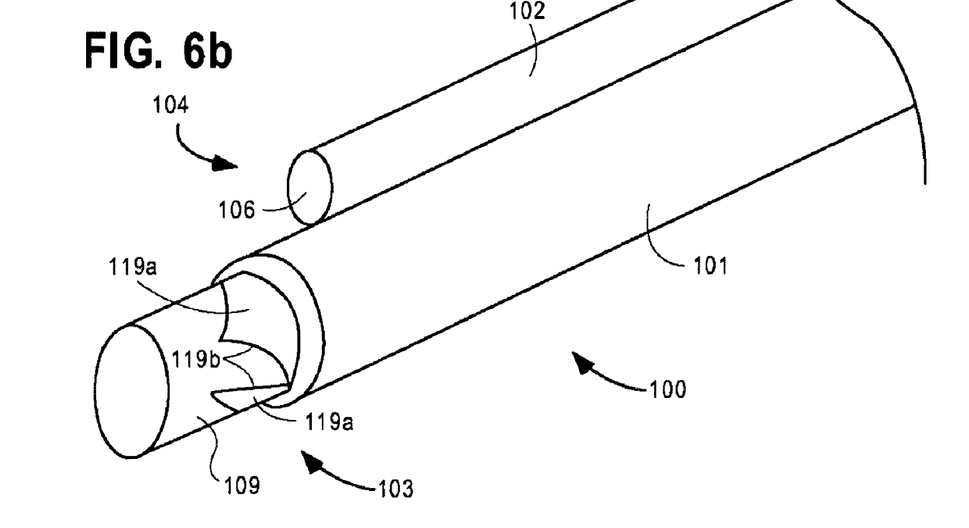

FIGS. 6a and 6b are side views of dual lumen device 100 wherein the condition of distal opening 103 is controlled, in accordance with the invention, by the operation of a one-way valve. The one-way valve can be of many different types, but in this embodiment, it includes flaps 119a separated from each other by slits 119b, which extend cross-wise. Flaps 119a extend inwardly from the outer periphery of distal opening 105 proximate to distal end 103. In FIG. 6a, instrument 109 is in its retracted position where it terminates inside of tube 101 before distal end 103. In FIG. 6b, instrument 109 is in its extended position wherein a portion of it extends outside of tube 101 beyond distal end 103.

When instrument 109 is in its retracted position, flaps 119a seal distal opening 105 so that the flow of matter therethrough is restricted. Further, adjacent flaps 119a engage each other so that slits 119b are closed. When instrument 109 moves from its retracted position to its extended position, it engages flaps 119a and they are moved away from distal opening 105 and beyond distal end 103 so that slits 119b open up. When instrument 109 is in its extended position, it engages flaps 119a and pushes them outwardly so they do not seal opening 105 and the flow of matter therethrough is not restricted by just them. Instead, the flow of matter through opening 105 is restricted by the width of instrument 109 and its engagement with the inner periphery of tube 101, as well as the engagement of the outwardly extending flaps with instrument 109.

Hence, instrument 109 is moveable between its extended and retracted positions and, in response, slits 119b move between their open and closed positions, respectively. In this way, flaps and slits 119a and 119b are used so that distal end 103 operates as a one-way valve in response to the movement of instrument 109.

Figure 7A:
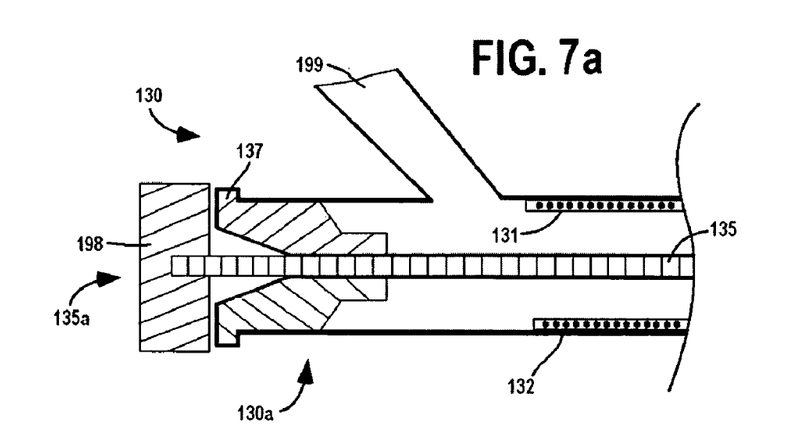
FIGS. 7a, 7b and 7c are side views of a dual lumen device, in accordance with the invention, having a nasal catheter.
Figure 7B:
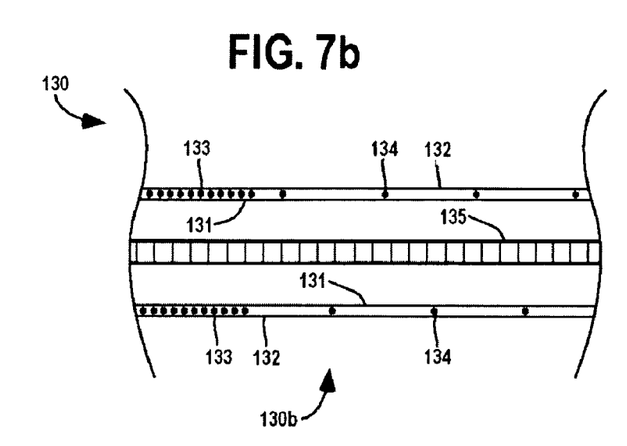
Figure 7C:
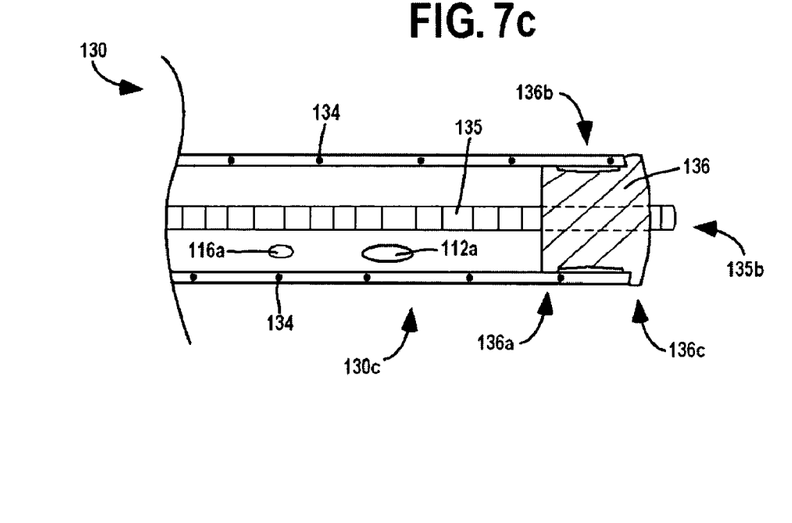

FIGS. 7a, 7b and 7c are side views of a catheter 130, in accordance with the invention. FIG. 7a is a side view of a proximal portion 130a of catheter 130, FIG. 7b is a side view of an intermediate portion 130b of catheter 130 and FIG. 7c is a side view of a distal portion 130c of catheter 130. In this embodiment, catheter 130 includes inner and outer tubes 131 and 132 which extend between its proximal and distal portions 130a and 130c. Inner and outer tubes 131 and 132 can be made of many different materials, but here tube 131 includes TEFLON® and tube 132 includes POLYURETHANE. In other embodiments, tube 132 can include TEFLON® and tube 131 can include POLYURETHANE. It should be noted that tube 131 extends through tube 132 so that they are coaxial. More information regarding coaxial tubes can be found in co-pending U.S. patent application Ser. No. 11/353,728, entitled PLURAL LUMEN GASTROSTOMY TUBE INSERT FOR PLACEMENT INTO THE DUODENUM AND METHOD OF MONITORING AND MANAGING FEEDING, filed on Feb. 13, 2006, by the same inventor, the contents of which are incorporated herein by reference.

In accordance with the invention, catheter 130 includes an aspiration tube 199 positioned proximate to proximal portion 130a. Aspiration tube 199 is in fluid communication with inner tube 131 so that aspiration can flow therebetween. Further, catheter 130 includes window 112a and aspirating orifice 116a positioned proximate to distal portion 130c. Window 112a and aspirating orifice 116a extend through inner and outer tubes 131 and 132 (FIG. 7c), and operate as described in more detail above. It should be noted that catheter 130 generally includes windows and orifices opposed to window 112a and orifice 116a, respectively, but these are not shown here for simplicity.

In accordance with the invention, catheter 130 includes springs 133 and 134 which extend between inner and outer tubes 131 and 132. In this embodiment, spring 133 extends between proximal portion 130a and intermediate portion 130b (FIGS. 7a and 7b). Further, spring 134 extends between intermediate portion 130c and distal portion 130c (FIGS. 7b and 7c). In this way, springs 133 and 134 extends through coaxial tubes.

In this embodiment, springs 133 and 134 include a different number of turns, wherein spring 133 includes more turns than spring 134. Springs 133 and 134 can extend many different lengths along inner and outer tubes 131 and 132. In one embodiment, spring 133 extends, in an unflexed condition, about ten to eighteen inches along tubes 131 and 132. Further, spring 134 extends, in an unflexed condition, about twenty to thirty inches along tubes 131 and 132.

In this embodiment, a feeding tube 135 extends through inner and outer tubes 131 and 132 (FIGS. 7a, 7b and 7c), wherein inner tube 131 is positioned between feeding tube 135 and outer tube 132. Feeding tube 135 includes an adapter 198 attached to its proximal end 135a. Further, a proximal plug 137 is engaged with catheter 130 proximate to its proximal portion 130a. In this embodiment, proximal plug 137 is frictionally engaged with outer tube 132 and has a central opening sized and shaped to allow feeding tube 135 to extend through it.

A distal end 135b of feeding tube 135 is connected to a distal plug 136, wherein distal plug 136 is sized and shaped to engage distal portion 130c of catheter 130. Distal plug 136 can engage catheter 130 in many different ways, such as by friction or an adhesive. In this embodiment, distal plug 136 includes proximal, distal and intermediate portions 136a, 136b and 136c, wherein proximal and distal portions 136a and 136b have a larger radial dimension than intermediate portion 136c. Distal plug 136 includes a central opening which extends through its proximal, distal and intermediate portions 136a, 136b and 136c. Proximal, distal and intermediate portions 136a, 136b and 136c extend away from the central opening of plug 136. Proximal and distal portions 136a and 136b extend further away from the central opening of plug 136 than intermediate portion 136c.

Distal plug 136 is generally inserted into distal portion 130c so that proximal portion 136a engages inner tube 131 proximate to window 112a and distal portion 136c engages inner tube 131 away from window 112a. In this way, distal plug 136 is frictionally engaged with inner tube 131. It should be noted that the central opening of distal plug 136 is sized and shaped so that feeding tube 135 can extend through it, as will be discussed in more detail presently.

In operation, distal plug 136 is engaged with distal portion 130b of catheter 130 and a medical instrument, such as an angioscope or gastroscope, is inserted through catheter 130 by extending it through inner tube 131. The medical instrument and catheter are then inserted into the patient through his or her nasal passage. In this way, the portion of catheter 130 between proximate and intermediate portions 130a and 130b are adjacent to the patient's nasal passage and the portion of catheter 130 between distal and intermediate portions 130b and 130c are adjacent to the patient's esophagus and stomach. It should be noted that the thicknesses of inner and outer tubes 131 and 132, as well as the spring constants and number of turns of springs 133 and 134, are chosen so that catheter 130 has a desired flexibility so they can be comfortably inserted into the patient.

The medical instrument is withdrawn from the patient and catheter 130, wherein catheter 130 is left in the patient, as described above. Proximal plug 137 is positioned so it engages proximal portion 130a. Feeding tube 135 is inserted into the patient by inserting it through the central opening of proximal plug 137 and into catheter 130 by extending it through inner tube 131. The insertion of feeding tube 135 into the patient and catheter 130 can be facilitated by using a guide-wire (not shown), wherein the guide-wire is then withdrawn. More information regarding the insertion of feeding tube 135 into a patient by using a guide-wire can be found in the co-pending U.S. patent application mentioned above.

Figure 8:
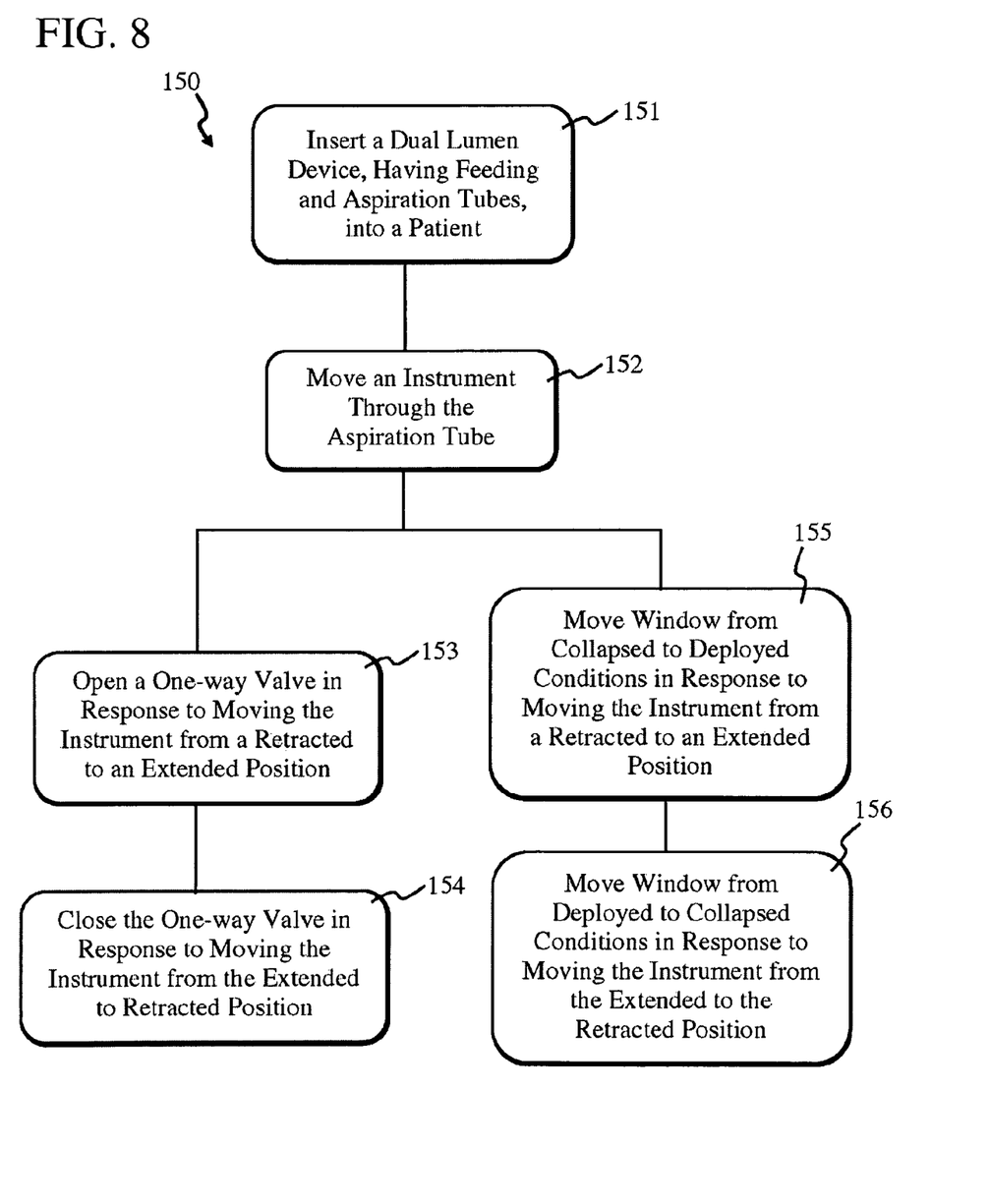
FIG. 8 is a flow diagram of a method of using a dual lumen gastrointestinal feeding and aspirating device, in accordance with the invention.

FIG. 8 is a flow diagram of a method 150 of using a dual lumen gastrointestinal feeding and aspirating device (dual lumen device), in accordance with the invention. It should be noted that the steps in method 150 can be carried out in many different orders. In this embodiment, method 150 includes a step 151 of inserting a dual lumen device into a patient. In accordance with the invention, the dual lumen device includes an aspiration tube which carries a feeding tube. In this embodiment, the aspiration tube has a larger sized distal opening than the feeding tube.

Method 150 also includes a step 152 of moving an instrument through the aspiration channel. In this embodiment, the diameter of the instrument is larger than the diameter of the feeding tube, but smaller than the diameter of the aspiration tube. Hence, the size of the distal opening of the feeding tube is too small to accommodate extending the instrument through it. However, the size of the distal opening of the aspiration tube is large enough to accommodate extending the instrument through it. In this way, the aspiration tube operates as a stent and allows the insertion of a larger diameter instrument into the patient than would otherwise be allowed.

In accordance with the invention, the distal end of the aspiration tube moves between open and closed conditions in response to the movement of the instrument. This can be done in many different ways. In one way, a one-way valve is attached to the aspiration tube proximate to its distal end to control the flow of matter through its distal opening. In a step 153, the one-way valve is opened in response to moving the instrument from a retracted position to an extended position through the one-way valve. In a step 154, the one-way valve is closed in response to moving the instrument from the extended position to the retracted position through the one-way valve.

Another way the distal end of the aspiration tube can be moved between open and closed conditions is by positioning windows proximate to its distal end. In a step 155, the windows move from collapsed to deployed conditions in response to moving the instrument from the retracted to the extended position. It should be noted that, in this embodiment, step 155 occurs after step 152. In a step 156, the windows move from deployed to collapsed conditions in response to moving the instrument from the extended to the retracted position. It should be noted that opposed windows are used in this embodiment, but, in general, one or more windows can be used and they may or may not be opposed. Further, they can be positioned at many different locations proximate to the distal end of the aspiration tube, as discussed in more detail above. Further, the distal opening of the aspiration tube can be biased to deploy and collapse in many different ways, several of which were discussed above.

Figure 9:
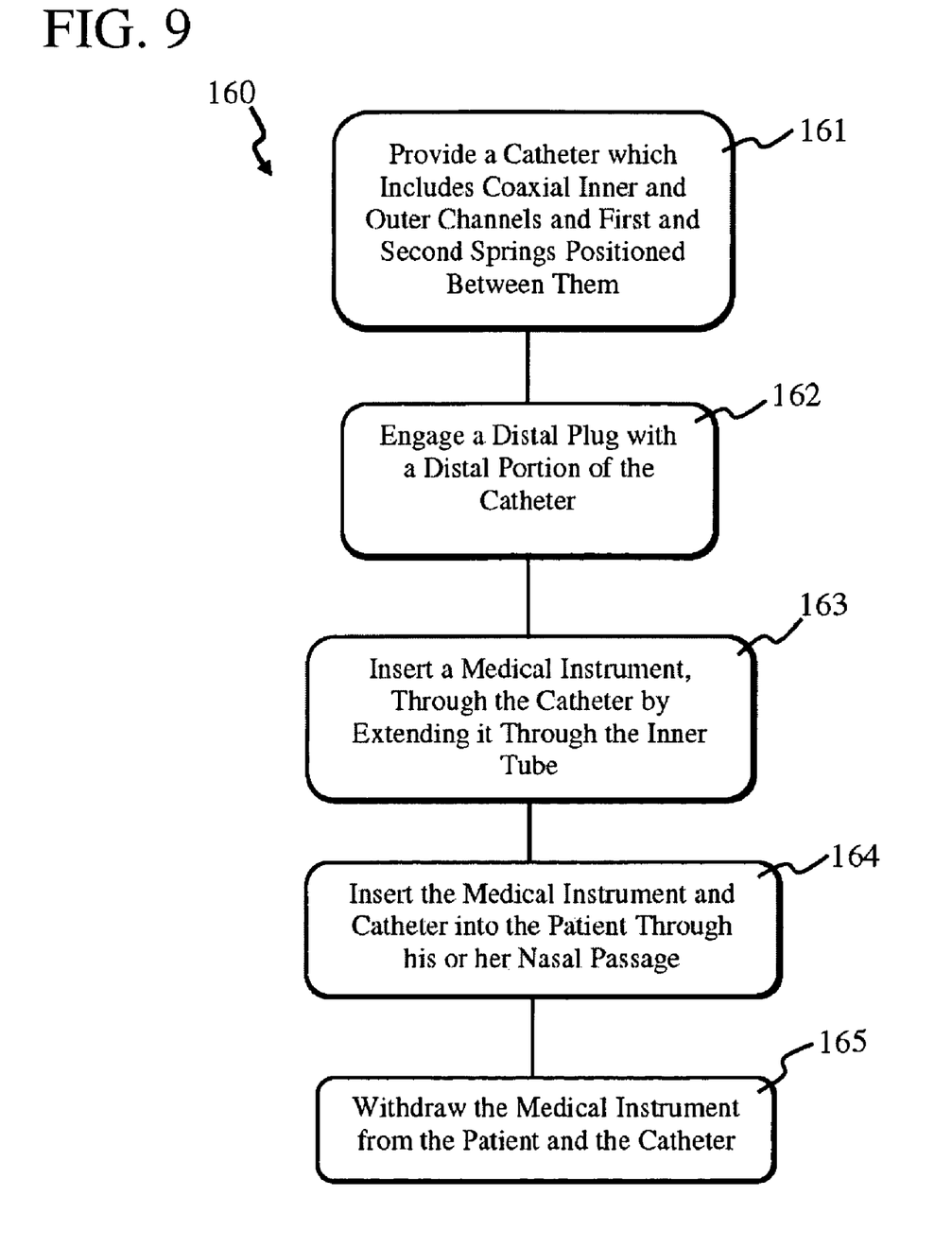
FIG. 9 is a flow diagram of a method of using a catheter, in accordance with the invention.

FIG. 9 is a flow diagram of a method 160 of using a catheter, in accordance with the invention. It should be noted that the steps in method 160 can be carried out in many different orders. In this embodiment, method 160 includes a step 161 of providing a catheter which includes coaxial inner and outer tubes and first and second springs positioned between them. The thicknesses of the inner and outer channels, as well as the spring constants and number of turns of the first and second springs, are chosen so that the catheter has a desired flexibility so they can be comfortably inserted into the patient. The first spring is positioned between a proximal and intermediate portion of the catheter and the second spring is positioned between the intermediate and a distal portion of the catheter.

Method 160 includes a step 162 of engaging a distal plug with a distal portion of the catheter and a step 163 of inserting a medical instrument, such as an angioscope or gastroscope, through the catheter by extending it through the inner tube. Method 160 includes a step 164 of inserting the medical instrument and catheter into the patient through his or her nasal passage. In this way, the portion of the catheter between its proximal and intermediate portions are adjacent to the patient's nasal passage and the portion of catheter between its distal and intermediate portions are adjacent to the patient's esophagus and stomach. Hence, the first spring is adjacent to the nasal cavity and the second spring is adjacent to the esophagus and stomach. In this embodiment, method 160 includes a step 165 of withdrawing the medical instrument from the patient and the catheter, wherein the catheter is left in the patient, as described above.

It should be noted that method 160 can include many other steps. For example, method 160 can include a step of positioning a proximal plug so it engages a proximal portion of the catheter. Method 160 can include a step of inserting a feeding tube into the patient by inserting it through a central opening of the proximal plug and into the catheter by extending it through the inner tube. The insertion of the feeding tube into the patient and the catheter can be facilitated by using a guide-wire (not shown), wherein the guide-wire is then withdrawn.

Figure 10:
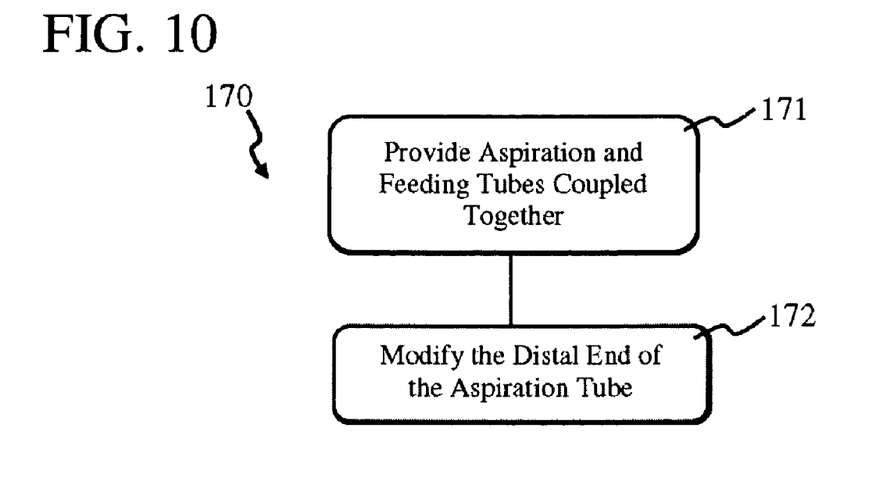
FIG. 10 is a flow diagram of a method of manufacturing a dual lumen gastrointestinal feeding and aspirating device, in accordance with the invention.

FIG. 10 is a flow diagram of a method 170 of manufacturing a dual lumen gastrointestinal feeding and aspirating device, in accordance with the invention. It should be noted that the steps of method 170 can be carried out in many different ways. In this embodiment, method 170 includes a step 171 of providing aspiration and feeding tubes coupled together. The aspiration and feeding tubes can be coupled together in many different ways. For example, in some embodiments, they are formed of a single integral piece and in other embodiments, they are formed separately and then fastened together, such as with an adhesive. In this way, the dual lumen device includes separate aspiration and feeding channels.

In accordance with the invention, the aspiration tube is larger than the feeding tube. Further, the aspiration tube has a circular cross-section and serves as a stent which allows the insertion of a larger size instrument into the patient. In some embodiments, the feeding tube is crescent shaped to reduce the cross-sectional area of the distal end of the dual lumen device.

In some embodiments, the feeding tube extends beyond the aspiration tube. Further, in some embodiments, the feeding tube has an elongated member attached to it. The elongated member can be grasped with forceps extending through the aspiration tube to facilitate the insertion of the dual lumen device into the patient.

In this embodiment, method 170 includes a step 172 of modifying the distal end of the aspiration tube so it is repeatably moveable between open and closed conditions in response to the extension and retraction, respectively, of the instrument through it. The distal end of the aspiration tube can be modified in many different ways. For example, in one embodiment, windows are positioned proximate to the distal end of the aspiration tube. The windows move away from each other in response to the movement of the instrument from a retracted position to an extended position. The distal end of the aspiration tube moves to its open condition in response to the advancement of the medical instrument. The windows move towards each other and collapse in response to suction provided by moving the medical instrument from its extended position to its retracted position. When the windows collapse, the distal opening of the aspiration tube is effectively occluded.

Another way the distal end of the aspiration tube can be modified is by connecting a one-way valve to it. The distal end of the aspiration tube is moved between its open and closed conditions in response to activating and deactivating, respectively, the one-way valve. The one-way valve is activated and deactivated in response to the extension and retraction, respectively, of the medical instrument through it.

Figure 11:
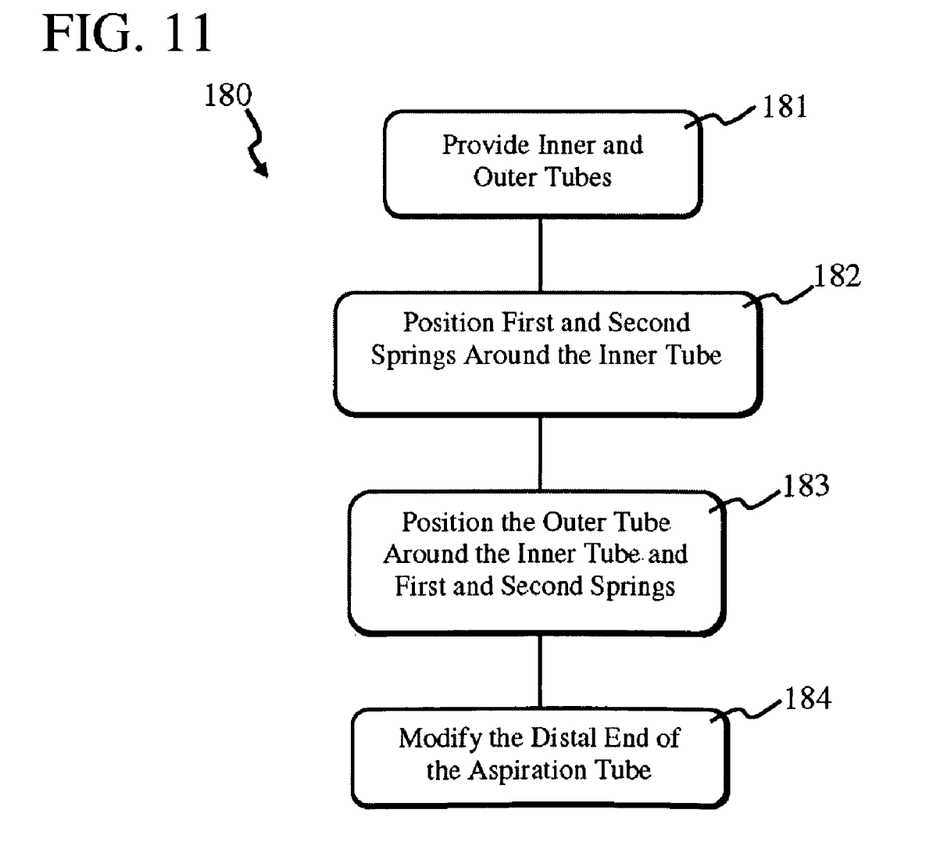
FIG. 11 is a flow diagram of a method of manufacturing a catheter, in accordance with the invention.

FIG. 11 is a flow diagram of a method 180 of manufacturing a catheter, in accordance with the invention. It should be noted that the steps of method 180 can be carried out in many different ways. In this embodiment, method 180 includes a step 181 of providing inner and outer tubes and a step 182 of positioning first and second springs around the inner tube. Method 180 includes a step 183 of positioning the outer tube around the inner tube and first and second springs. In this way, the first and second springs are positioned between the inner and outer tubes. The first spring is positioned between a proximal and intermediate portion of the catheter and the second spring is positioned between the intermediate and a distal portion of the catheter. Method 180 includes a step 184 of modifying the distal end of the catheter so it is repeatably moveable between open and closed conditions in response to the extension and retraction, respectively, of the instrument through it. The distal end of the catheter can be modified in many different ways, such as by forming one or more windows which extend through the inner and outer tubes. The distal end of the catheter can also be modified by connecting a one-way valve to it. It should be noted that method 180 can include many other manufacturing steps. For example, in some embodiments, an aspiration tube is connected to the catheter proximate to its proximal end, wherein the aspiration tube is in fluid communication with the inner tube.

The embodiments of the invention described herein are exemplary and numerous modifications, variations and rearrangements can be readily envisioned to achieve substantially equivalent results, all of which are intended to be embraced within the spirit and scope of the invention.

The invention claimed is:
1. A method, comprising:
   inserting a dual lumen gastrointestinal device into a patient, the dual lumen gastrointestinal device including an aspiration tube which carries a feeding tube, the aspiration tube having a larger sized distal opening than the feeding tube;
   inserting the dual lumen gastrointestinal device through the patient's nasal passage; and
   moving an instrument through the aspiration tube, wherein the distal opening of the aspiration tube moves between deployed and collapsed conditions in response to movement of the instrument, wherein the aspiration tube includes a window positioned proximate to a distal end of the aspiration tube and further wherein the instrument is selected from the group consisting of a gastroscope and/or an angioscope.

2. The method of claim 1, wherein a distal opening of the aspiration tube is spaced a distance from a distal opening of the feeding tube.

3. The method of claim 1, wherein the size of a distal opening of the feeding tube is too small to accommodate extending the instrument through it.

4. The method of claim 1, further including collapsing the distal opening of the aspiration tube with suction provided by movement of the instrument.

5. The method of claim 1, further including collapsing the window in response to movement of the instrument.

6. The method of claim 1, wherein the aspiration and feeding tubes are external to each other.

7. The method of claim 1, wherein a portion of the aspiration tube proximate to its distal opening is coupled to the feeding tube.

8. A method, comprising:
providing a dual lumen gastrointestinal device, the dual lumen gastrointestinal device including an aspiration tube which carries an external feeding tube, wherein the aspiration tube includes a window positioned proximate to its distal end;
inserting the dual lumen gastrointestinal device into a patient through the patient's nasal passage; and
moving an instrument through the aspiration tube, wherein the window moves between deployed and collapsed conditions in response to movement of the instrument, wherein the instrument is selected from the group consisting of a gastroscope and/or an angioscope.

9. The method of claim 8, wherein a distal opening of the aspiration tube moves between deployed and collapsed conditions in response to the window moving between deployed and collapsed conditions, respectively.

10. The method of claim 8, wherein the distal end of the aspiration tube moves between open and closed conditions in response to the window moving between the deployed and collapsed conditions, respectively.

11. The method of claim 8, wherein a distal opening of the feeding tube is tapered.

12. The method of claim 8, wherein a distal opening of the aspiration tube is spaced from the distal opening of the feeding tube.

13. The method of claim 8, wherein the width of the instrument is too large to extend through the feeding tube.

14. The method of claim 8, wherein the aspiration tube has a larger sized distal opening than the feeding tube.

15. The method of claim 8, wherein the dual lumen gastrointestinal device further includes an elongated member with one end coupled to the feeding tube, wherein the elongated member includes a string.

16. The method of claim 8, wherein the distal openings of the aspiration and feeding tubes are positioned contiguously adjacent each other.

17. A method, comprising:
providing a dual lumen gastrointestinal device, the dual lumen gastrointestinal device including an aspiration and feeding tube, wherein the aspiration tube has a larger sized distal opening than the feeding tube;
inserting the dual lumen gastrointestinal device into a patient through the patient's nasal passage; and
moving an instrument through the aspiration tube, the distal opening of the aspiration tube moving between open and closed conditions in response to movement of the instrument, wherein the instrument has a dimension which prevents it from extending through a distal opening of the feeding tube and the instrument is selected from the group consisting of a gastroscope and/or an angioscope.

18. The method of claim 17, wherein the aspiration tube includes opposed windows positioned proximate to its distal end.

19. The method of claim 18, wherein the opposed windows move between deployed and collapsed conditions in response to movement of the instrument.

20. The method of claim 19, wherein the distal opening of the aspiration tube moves between deployed and collapsed conditions in response to the window moving between deployed and collapsed conditions, respectively.

21. The method of claim 18, wherein the opposed windows move towards and away from each other in response to movement of the instrument.

22. The method of claim 17, wherein the aspiration tube includes a plurality of aspirating orifices.

23. The method of claim 17, wherein the distal opening of the aspiration tube is spaced from the distal opening of the feeding tube.

24. The method of claim 17, wherein the opposed windows are positioned past the distal end of the feeding tube.

25. The method of claim 17, wherein the feeding tube is external to the aspiration tube.

* * * * *